(12) United States Patent
Nanda et al.

(10) Patent No.: US 11,224,451 B2
(45) Date of Patent: Jan. 18, 2022

(54) FORCEPS

(71) Applicant: OCuSOFT, Inc., Rosenberg, TX (US)

(72) Inventors: Seema Nanda, Houston, TX (US);
Troy Smith, Rosenberg, TX (US)

(73) Assignee: OCuSOFT, Inc., Rosenberg, TX (US)

( * ) Notice: Subject to any disclaimer, the term of this patent is extended or adjusted under 35 U.S.C. 154(b) by 91 days.

(21) Appl. No.: 16/565,781

(22) Filed: Sep. 10, 2019

(65) Prior Publication Data

US 2020/0078032 A1 Mar. 12, 2020

Related U.S. Application Data

(60) Provisional application No. 62/729,256, filed on Sep. 10, 2018.

(51) Int. Cl.
| *A61B 17/29* | (2006.01) |
| *A61F 9/007* | (2006.01) |
| *A61B 17/28* | (2006.01) |

(52) U.S. Cl.
CPC ............ *A61B 17/29* (2013.01); *A61B 17/282* (2013.01); *A61F 9/00709* (2013.01); *A61B 2017/2926* (2013.01)

(58) Field of Classification Search
CPC ....... A61B 17/282; A61B 17/29; A61B 17/30; A61B 2017/2926; A61F 9/00709; A61C 3/14
USPC ............. 294/99.2; 433/162; 606/205, 210
See application file for complete search history.

(56) References Cited

U.S. PATENT DOCUMENTS

| 4,728,139 A | 3/1988 | Oretti |
| 5,019,091 A * | 5/1991 | Porat ...................... A61B 17/30 606/205 |
| 6,517,554 B1 * | 2/2003 | Zhu ........................ A61B 17/30 606/150 |
| 2002/0106609 A1 | 8/2002 | Palermo et al. |
| 2002/0127514 A1 * | 9/2002 | Dietrich .................. A61C 3/10 433/159 |
| 2004/0181240 A1 | 9/2004 | Tseng et al. |

FOREIGN PATENT DOCUMENTS

| CN | 201171700 Y | 12/2008 |
| CN | 202355448 U | 8/2012 |
| RU | 2319475 C2 | 3/2008 |

\* cited by examiner

*Primary Examiner* — Brooke Nicole Labranche
(74) *Attorney, Agent, or Firm* — D'Ambrosio & Menon, PLLC; Usha Menon

(57) ABSTRACT

The invention involves forceps having rounded grasping tips. The rounded tips are configured to avoid puncturing an amniotic membrane during insertion over an ocular surface for the treatment of dry eye disease and inflammation of the eyes and to avoid injuring the conjunctiva during removal of an amniotic membrane from the ocular surface. The forceps have grasping tips at its distal end, wherein one of the grasping tips has a notch on its inside surface. The dimensions of the notch are configured to permit an eye doctor to securely and safely grasp a lip of an amniotic membrane insert for better insertion and removal from an ocular surface.

9 Claims, 6 Drawing Sheets

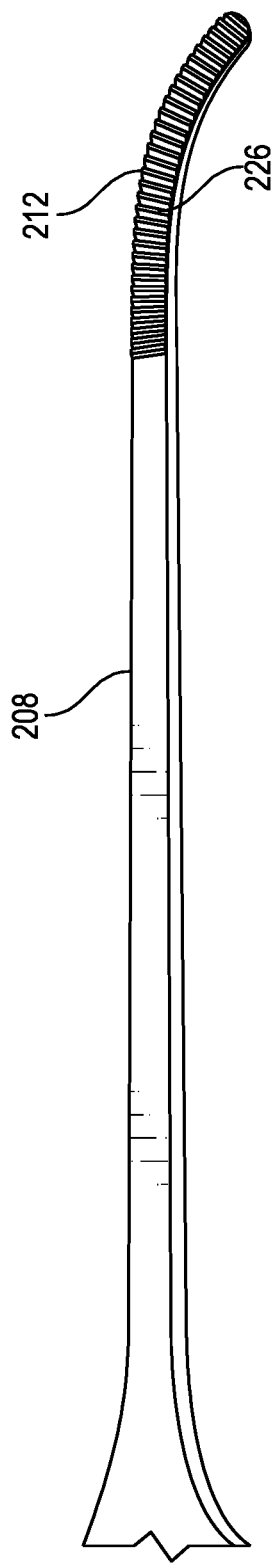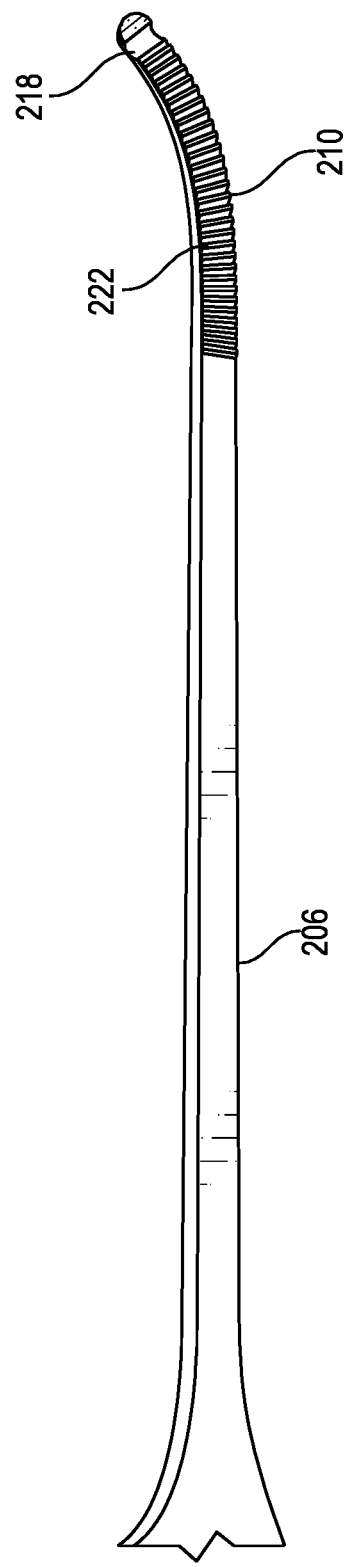

FORCEPS

CROSS-REFERENCE TO RELATED APPLICATION

This application claims the benefit of Provisional U.S. Patent Application No. 62/729,256, filed Sep. 10, 2018, entitled "FORCEPS", the entire content and disclosure of which, both express and implied, is incorporated herein by reference.

BACKGROUND OF THE INVENTION

Field of the Invention

The present invention relates generally to surgical implements for gripping an amniotic membrane, and more particularly to forceps for use by eye doctors.

Background

The eyes produce tears to stay moist. Tears are necessary for maintaining the health of the front surface of the eye and for providing clear vision. Tears provide lubrication, reduce the risk of eye infection, wash away foreign matter in the eye and keep the surface of the eyes smooth and clear. Excess tears in the eyes flow into small drainage ducts in the inner corners of the eyelids, which drain into the back of the sinuses. However, if the eyes do not make sufficient tears or something affects one or more layers of the tear film, we can end up with dry eyes.

Dye eye syndrome or dry eye disorder (DED) is a common ocular surface disorder. DED affects a significant percentage of the population. Its symptoms include ocular discomfort and visual fluctuations. Ocular inflammation is a common factor in DED. This in turn induces further damage to the corneal epithelium and its underlying structures. Various treatment modalities, such as steroids and cyclosporine, have been used to suppress inflammation. However, results are variable and refractory in some cases. In these cases, DED not only negatively impacts the quality of life, but also increases the burden on health economics.

Progress has been made in understanding the pathogenesis of DED, and different treatment modalities have been introduced. Cryopreserved amniotic membrane has been used recently to treat DED with ocular surface involvement. The amniotic membrane (AM) is the innermost lining of the placenta (amnion). The AM can accelerate the recovery of corneal surface health in patients with moderate and severe DED. The therapeutic effect of the AM in the treatment of DED can be attributed to multiple mechanisms of action. For instance, the AM acts as a therapeutic bandage that keeps the eye moist by retaining tears and protects the ocular surface from the surrounding environment. Additionally, AM controls ocular surface inflammation since it is well established that inflammation triggered by both innate and adaptive immune responses is critical to the pathogenesis and chronicity of DED.

Currently, the AM is inserted into the eye using fingers or conventional forceps and brought into the subconjunctival space where it is then evenly distributed. However, the AM is typically removed from the eyes using swab sticks or non-toothed, smooth conventional forceps. When the AM is grasped with conventional forceps, the distal end of the forceps can injure the bulbar conjunctiva, which covers the outer surface of the eye. Accordingly, forceps which can facilitate secure and convenient insertion and removal of AM to cover the ocular surface becomes necessary.

SUMMARY

The invention involves forceps having rounded grasping tips that are configured to avoid puncturing the amniotic membrane during insertion over an ocular surface. When the time period for treatment of inflammation of the eyes due to dry eyes or other corneal disorder arises, the forceps are used to avoid injuring the conjunctiva during removal of an amniotic membrane from the ocular surface. On one side of the forceps, there is a notched area on the inside surface of the tip. The notched surface is configured to permit an eye doctor to securely and safely grasp a lip of the amniotic membrane for better removal. On the other side are grooves to lock the AM into place to avoid slippage.

One embodiment of the present invention includes a forceps comprising: a proximal end; a distal end; a first arm; a second arm having the same length as the first arm, wherein the first and second arms are connected at the proximal end and have blunt, rounded distal ends; a first gripping portion positioned between the proximal end and the distal end of the first arm and a second gripping portion positioned between the proximal end and the distal end of the second arm; a first grasping tip adjacent the distal end of the first arm and a second grasping tip adjacent the distal end of the second arm; and an inner portion of the first grasping tip comprises a notch for grasping an edge of an amniotic membrane (insert).

Another embodiment of the present invention includes an ophthalmic forceps comprising: a first arm; a second arm having the same length and width as the first arm, wherein the first and second arms are connected at a proximal end and narrow as they pass from a proximal to a distal end; a blunt, rounded distal end of both the first and second arms; a first grasping tip adjacent the distal end of the first arm and a second grasping tip adjacent the distal end of the second arm, wherein the distal ends of the first and second grasping tips are curved downward from a horizontal axis of the forceps; and an inner portion of the first grasping tip comprises a notch dimensioned to grasp an edge of an amniotic membrane (insert).

Yet another embodiment of the present invention includes a method for removing a cryopreserved amniotic membrane insert from an ocular surface comprising: (a) putting a drop of anesthetic in an eye having an amniotic membrane insert sitting on an ocular surface of the eye to decrease the blink reflex; (b) providing a forceps having a first arm and second arm having the same length and width connected at a proximal end, a first grasping tip adjacent a distal end of the first arm, a second grasping tip adjacent a distal end of the second arm wherein the distal ends of the first and second grasping tips are curved downward from a horizontal axis of the forceps, blunt, rounded distal ends of the first and second grasping tips, and an inner portion of the first grasping tip having a notch dimensioned to grasp an edge of an amniotic membrane insert; (c) pulling downward on a lower eyelid to expose a portion of the amniotic membrane insert; (d) holding an inner ring of the AM within the notch of the first grasping tip; (e) squeezing the first and second arms together by hand to bring the first and second grasping tips towards each other thereby locking the AM into place within the notch and the grooved anti-transversal elements on the opposing grasping tip to avoid slippage; and (e) gently removing the amniotic membrane insert by the inner ring without damaging the cornea.

It will be apparent to those skilled in the art that the conception and the specific embodiments disclosed might be readily utilized as a basis for modifying or redesigning the structures for carrying out the same purposes as the invention. It should be realized by those skilled in the art that such equivalent constructions do not depart from the spirit and scope of the invention as set forth in the appended claims.

DRAWINGS

For a more complete understanding of the present invention, and the advantages thereof, reference is now made to the following description taken in conjunction with the accompanying drawings, in which:

FIG. 5 is a side view of one embodiment of the inner surface of a first grasping tip of the forceps shown in FIG. 4.

FIG. 6 is a side view of one embodiment of the inner surface of the second grasping tip of the forceps shown in FIG. 4.

DETAILED DESCRIPTION

Figure 1:
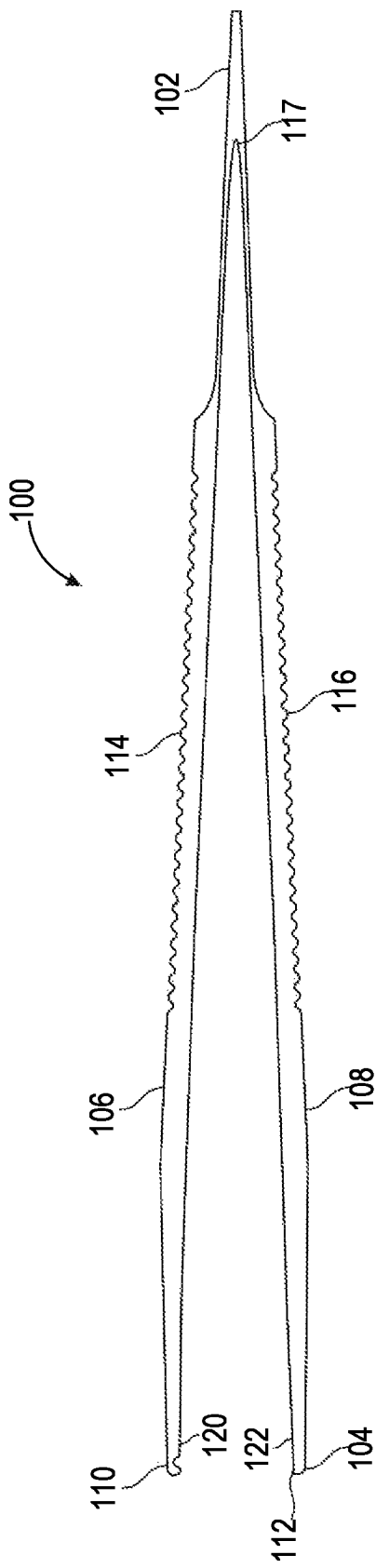
FIG. 1 is a top view of an exemplary embodiment of a forceps of the invention.

It is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in any appropriately detailed structure.

It is pointed out that like reference characters designate like or similar parts throughout the drawings. The figures, or drawings, are not intended to be to scale. For example, purely for the sake of greater clarity in the drawings, component size and spacing are not dimensioned as they actually exist in any of the assembled embodiments.

The invention relates generally to surgical implements for gripping amniotic membrane, and more particularly to forceps for use by eye doctors. As used herein, the term amniotic membrane or AM includes, without limitation, amniotic membrane, amniotic membrane insert, biological tissue and implant. The amniotic membrane can be cryopreserved amniotic membrane, such as, PROKERA®.

Referring now to FIG. 1, an exemplary embodiment of forceps 100 having a proximal end 102 and a distal end 104 will be described. Forceps 100 comprises a pair of arms 106, 108 which are connected at the proximal end 102. The arms 106, 108 are of equal length and width. Each of the arms includes a grasping tip portion 110, 112 near the distal end 104. The exterior/upper surface of an intermediate portion 114, 116 of each of the arms 106, 108 is provided with a plurality of grooved transversal anti-slip elements. As used herein, the term "grooved transversal anti-elements" means a groove located on either side of the anti-slip element. The intermediate portions 114, 116 are located between the proximal and distal ends. The anti-slip elements can include ridges, corrugations, or serrations. The anti-slip elements facilitate a smooth and slip-resistant grip of the forceps 100. The arms 106, 108 are coupled at a coupling section 117. However, in another embodiment (not shown), the intermediate portions can be smooth. The intermediate portions 114, 116 can be gripped and squeezed to bring arms 106, 108 toward each other. Optionally, the arms 106, 108 may narrow as they pass from the intermediate portions 114, 116 to the distal end 104.

The grasping tip portions 110, 112 have substantially rounded ends. The rounded ends are blunted and can ensure that the cornea is not injured during a surgical procedure. A bottom/interior surface of the grasping tip 110 includes a notch 118. The notch 118 is located proximal the distal end 104. As used herein, the term "notch" encompasses, without limitation, a notch, an indentation, a groove or a cutout portion on the interior surface of the forceps. The interior surface of the opposing grasping tip 112 is devoid of notches, that is, it does not include any notches.

Figure 2:
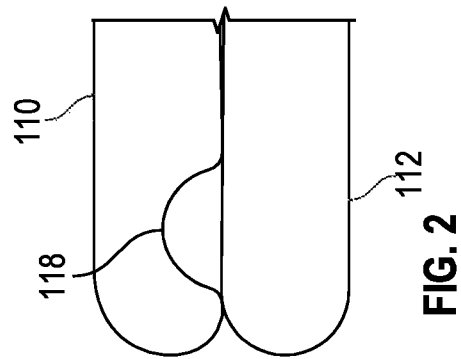
FIG. 2 is a side view illustrating the grasping tips of the forceps having a notch on an inner surface according to an embodiment of the invention.

An enlarged view of the notch 118 is depicted in FIG. 2. The notch 118 permits doctors to easily and securely grasp an edge of an amniotic membrane for efficient and non-injurious manipulation. The notch 118 is typically rounded with the height and width of the notch selected to fit an edge of the amniotic membrane that is desired to be removed or manipulated with the forceps. The notch 118 transverses the entire width of the grasping tip and is rounded or semi-circular in shape.

Figure 3:
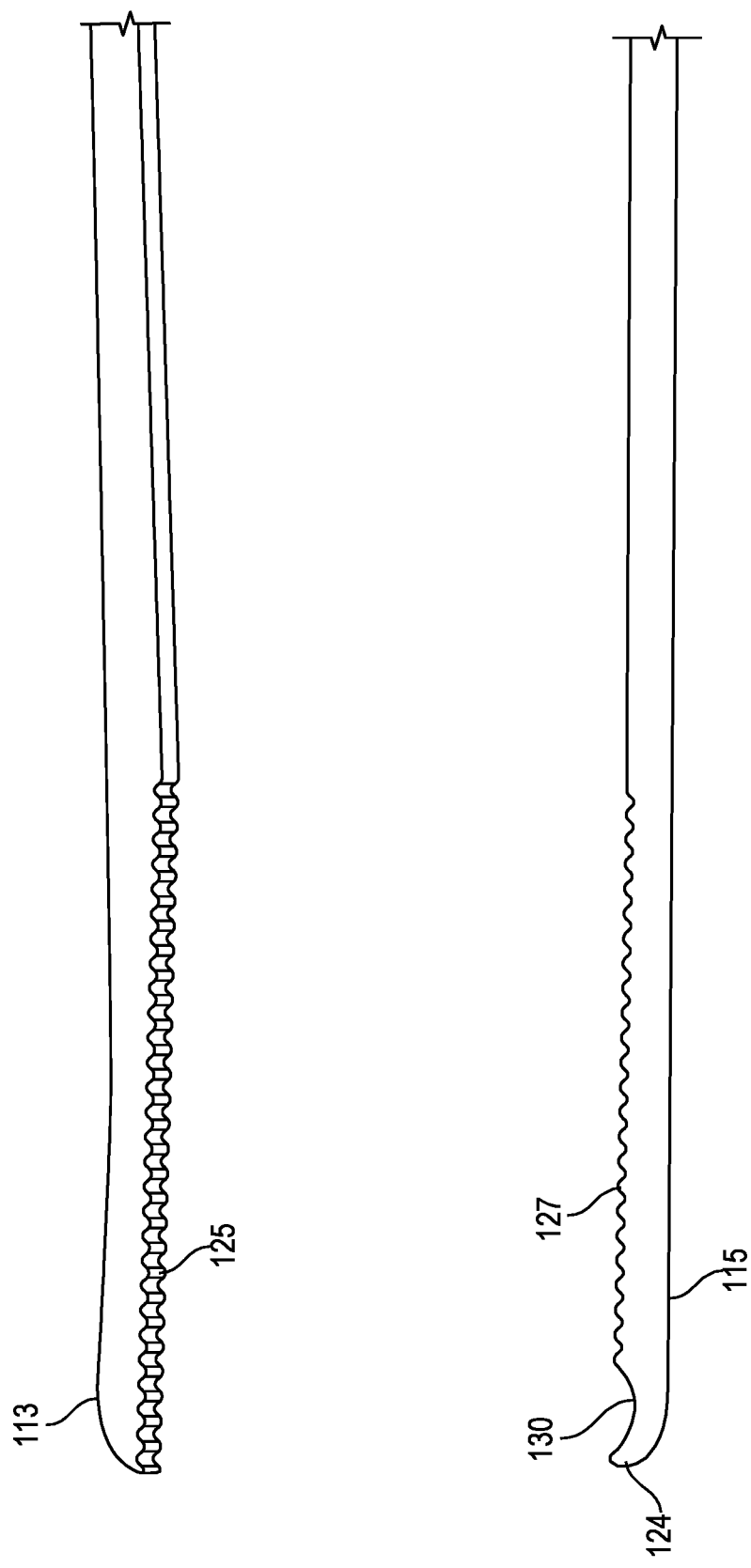
FIG. 3 is a side view illustrating the grasping tips of the forceps having a notch on an inner surface according to another embodiment of the invention.

FIG. 3 illustrates forceps similar to those illustrated in FIG. 1, except for the configuration of inner surfaces of the grasping tips. The embodiment of the forceps shown in FIG. 3 has an inner surface 125 of grasping tip 113 that is provided with a plurality of grooved transversal anti-slip elements, including, ridges, corrugations, or serrations. The inner surface 127 of the grasping tip 115 is similar except for a notch 130 proximal the distal end 124.

Figure 4:
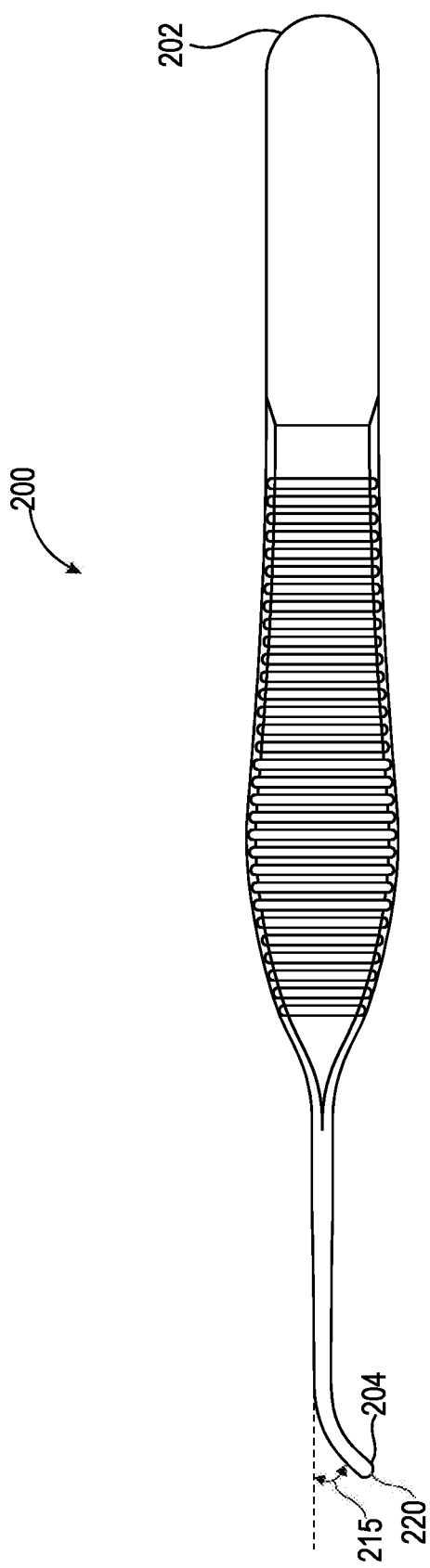
FIG. 4 is a side view of yet another embodiment of the forceps of the invention with curved grasping tips having blunt rounded tips.

Another embodiment of the forceps is shown in FIGS. 4-6. Forceps 200 have a proximal end 202 and a distal end 204. Forceps 200 comprises a pair of arms 206, 208 which are connected at the proximal end 202. The arms 206, 208 are of equal length and width. Each arm has a blunt, rounded tip at the distal end 204.

Arms 206, 208 will generally have gripping portions, similar to those described for forceps 100, formed as a unitary member by coupling the arms near the proximal end 202. The exterior/upper surface of an intermediate portion of each of the arms 206, 208 is provided with a plurality of grooved transversal anti-slip elements. The intermediate portions are located between the proximal and distal ends. The anti-slip elements can include ridges, corrugations, or serrations. The anti-slip elements facilitate a smooth and slip-resistant grip of the forceps 200. However, in another embodiment (not shown), the gripping portions can be smooth. The arms 206, 208 are coupled at a coupling section adjacent the proximal end. The arms may narrow as they pass from the intermediate portions to the distal end.

Forceps 200, as shown in FIG. 4, is similar to forceps 100 of FIG. 1 except for the configuration of the distal portion of the arms. As shown, the distal ends 220 of the arms are curved downward from the horizontal axis of the forceps. The angle of curvature 215 of the arms at their distal tips 220 is typically between 10° and 60°. The first and second grasping tip portions 210, 212, like the grasping tips 110, 112, have substantially rounded ends to decrease the risk of injury during a surgical procedure.

The inner/inside surface 222, 226 of the grasping tips 210, 212 are generally provided with a plurality of grooved transversal anti-slip elements, including, ridges, corrugations, or serrations. The interior/inside surface 222 of first grasping tip 210 includes a notched area/notch 218 proximal the distal end 204. The notch 218 is similar to notches 118 and 130. The notched area 218 is designed to fit an edge of a specific amniotic membrane to be held or manipulated during a particular procedure. The second grasping tip 212 has a plurality of grooved transversal anti-slip elements. The amniotic membrane can be securely locked into place between the notched area 218 and the grooved transversal anti-slip elements on the second grasping tip portion 212. The notched area 218 may vary in depth and width. One embodiment of the notch 218 transverses the entire width of the arm 210 and is rounded or semi-circular in shape. The dimension of the notch 118, 130, 218 is selected to optimize its ability to securely hold the amniotic membrane. The inner surface of the notch 218 may be smooth. However, the inner surface of the notch can also include one or more anti-slip elements.

The forceps of the present invention are preferably constructed of a resilient, corrosion-resistant material, such as stainless steel, platinum or another surgical grade material or alloy. The forceps are configured to be held conveniently between the fingers of either hand. The forceps can be between 140 mm-165 mm in length. The notch can have an inside diameter of 0.1 mm-5 mm. In one embodiment, the inside diameter of the notch is between 0.8 mm-1.8 mm.

In one or more embodiments, the rounded tips of the forceps can be enclosed within a protective cover (not shown). The cover can include vents or openings.

Another embodiment of the invention relates to a kit containing the forceps of the present invention as disclosed herein. The kit can also include one or more protective tip covers and instructions for using the forceps.

Figure 7:
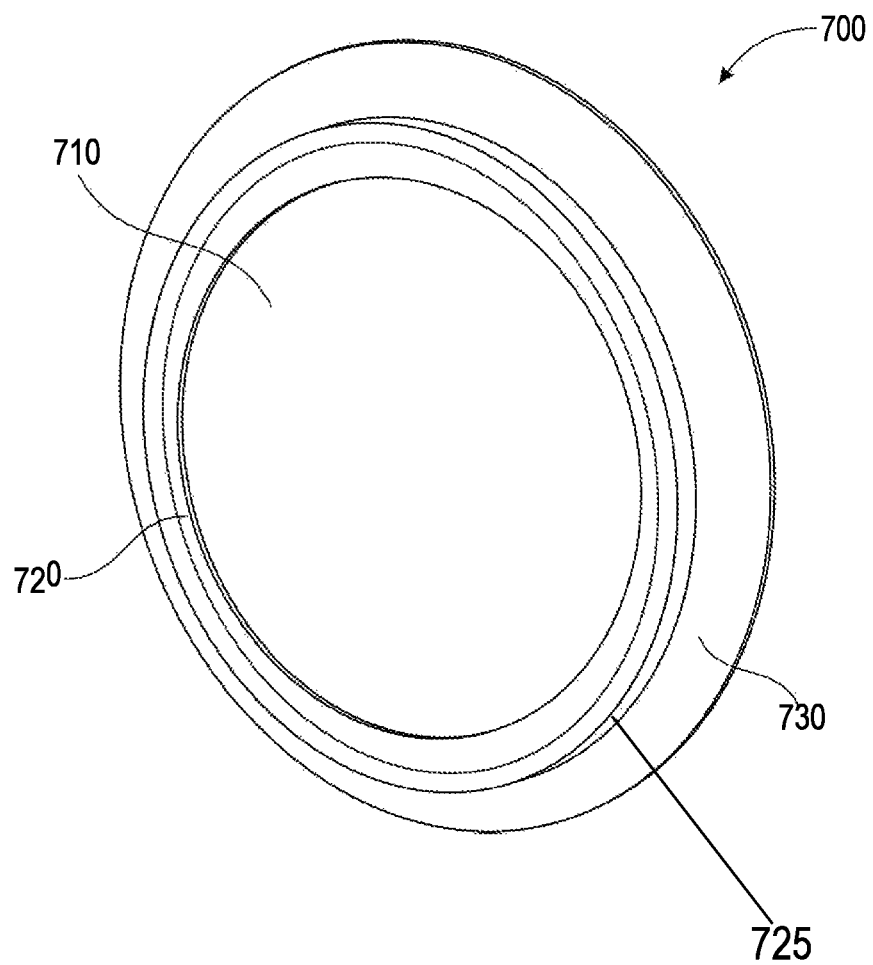
FIG. 7 is a perspective view of an amniotic membrane insert.

According to an embodiment, the forceps 200 can be used in the treatment of damaged eye surfaces. The treatment can involve using a cryopreserved amniotic membrane insert 700, such as, PROKERA®. As shown, in FIG. 7, the amniotic membrane insert 700, includes a piece of amniotic membrane 710 located within conformer rings—an inner ring 720 and an outer ring 730 set. The inner ring 720 includes an outer edge 725. The edge 725 can be held within the notch of the first grasping tip and locked in position within the forceps by the grooved transversal anti-slip elements on the second grasping tip. The rings can be made of a flexible, elastomeric material.

Conventionally, amniotic membrane insert 700 can be placed in the eye using the finger tips. However, in an exemplary embodiment, forceps 200 can be used to place amniotic membrane insert 700 onto the ocular surface. Advantageously, the forceps 200 also allow the doctor to securely grasp the amniotic membrane insert without puncturing/damaging it. The method involves putting a drop of topical anesthetic in the eye to numb it and to make the procedure more comfortable for the patient. The amniotic membrane insert 700 is removed from its cover and rinsed with a physiological saline. Using forceps 200, the eye doctor can grasp the inner ring 720 with the grasping tips 210, 212. The eye doctor then holds the upper eyelid of the patient up and asks the patient to look down. A portion of the amniotic membrane is place on the superior conjunctival fornix. This is followed by tucking the upper portion of the amniotic membrane 700 under the upper eyelid using the blunt and rounded ends of the forceps 200. Finally, the lower portion of the amniotic member is tucked under the lower eyelid.

The amniotic membrane 710 is typically dissolved, wholly or partially, within a few days. The amniotic membrane facilitates healing of the eye. The conformer rings and any remaining amniotic membrane can be removed from the ocular surface. Conventionally, amniotic membrane insert 700 is removed using the fingers or forceps. Conventional forceps are blunt forceps designed to remove therapeutic inserts by lifting the amniotic membrane insert from the outer ring or lower edge. Since the inside surface of the outer ring contacts the cornea, a common side effect of current removal methodologies using conventional forceps or instruments is the inadvertent prodding of the patient's cornea by the distal ends of the forceps causing damage or other injury to the bulbar conjunctiva which covers the outer surface of the eye.

Figure 8:
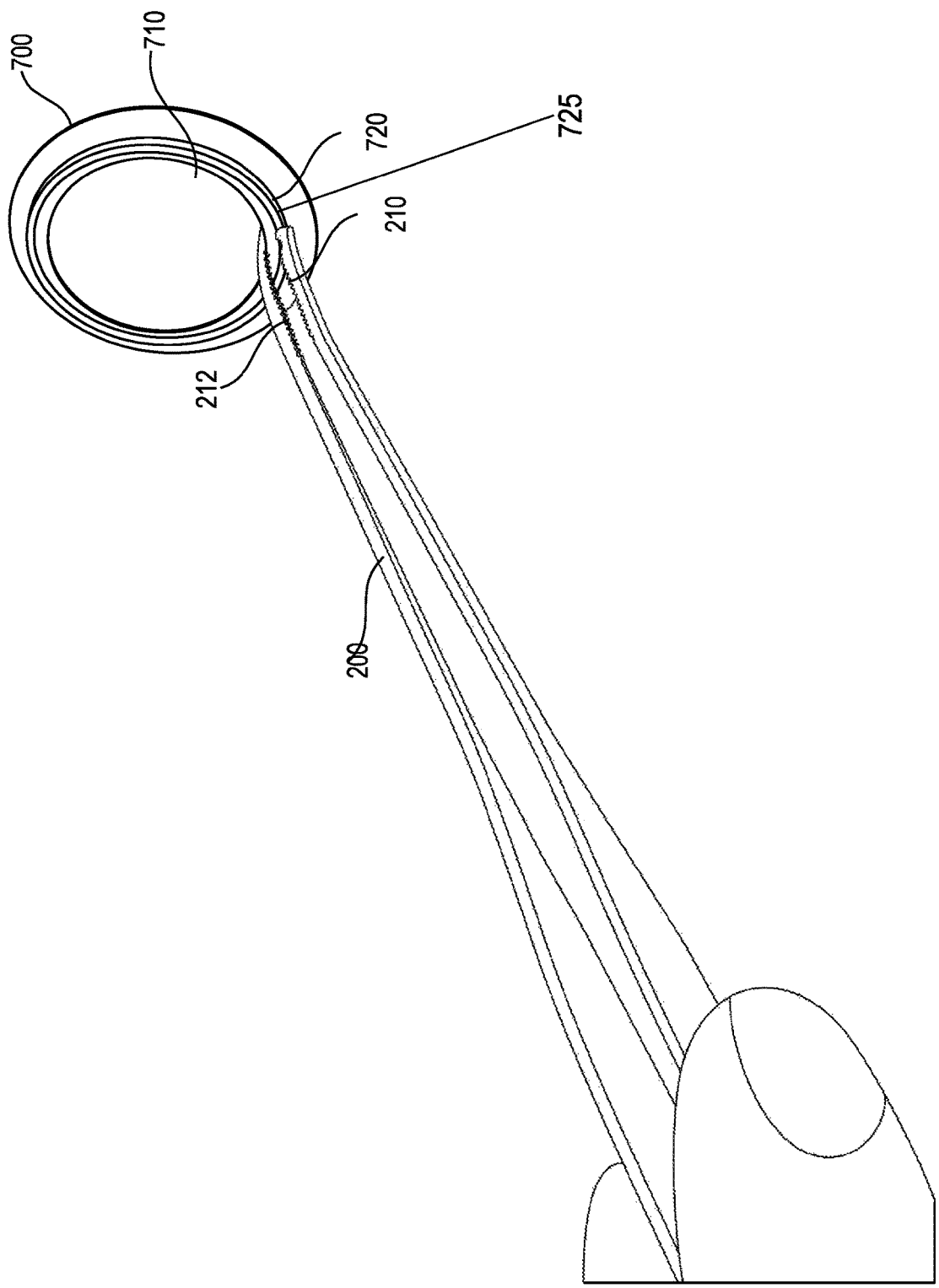
FIG. 8 shows the forceps shown in FIG. 4 grasping the amniotic membrane insert of FIG. 7.

The forceps of the current invention avoid causing such injury to the cornea. According to an embodiment, as shown in FIG. 8, forceps 200 can be used to remove amniotic membrane insert 700.

The method involves instilling a drop of anesthetic in the eye to make the removal procedure more comfortable for the patient. For example, the anesthetic can reduce the blink reflex in the patient when the eye doctor approaches the eye with the forceps 200. The eye doctor can pull downward on the lower eyelid to expose a portion of the amniotic membrane insert 700. Grasping tip portion 212 is placed on an inner edge of the inner ring 720 while grasping tip portions 210 is moved toward the edge 725 of the inner ring 720. The forceps 200 can be squeezed toward each other such that notch (218) can hold the inner ring by edge 725. The inner ring is locked in position within the forceps between the notch on the first grasping tip and the grooved transversal anti-slip elements on the second grasping tip. The amniotic membrane insert 700 can then be gently removed from its upper edge (or inner ring), as shown in FIG. 9. This is the opposite of conventional methods which involve the removal of the amniotic membrane insert 700 from its lower edge (or outer ring). Advantageously, the amniotic membrane insert can be removed without touching the cornea. Since the edge 725 of the inner ring 720 rises above the top surface of the outer ring 730, the forceps can grasp the inner ring to remove the amniotic membrane insert 700 without touching the cornea.

It is understood that, although the terms first, second, inside, outside, etc. are used herein to describe various surfaces, etc., these surfaces should not be limited by these terms. These terms are only used to distinguish one surface from another surface.

It will be apparent to those skilled in the art that the conception and the specific embodiments disclosed might be readily utilized as a basis for modifying or redesigning the structures for carrying out the same purposes as the invention. It should be realized by those skilled in the art that such equivalent constructions do not depart from the spirit and scope of the invention as set forth in the appended claims.

We claim:

1. An ophthalmic forceps for gripping an amniotic membrane insert, comprising:
   a first arm, the first arm comprising a first grasping tip adjacent a distal end of the first arm, the first arm further comprising a notch located along an inside surface of the first grasping tip, the notch being a rounded indentation in the inside surface having a width and a depth configured to fit an outer edge of an inner conformer ring on an amniotic membrane insert, wherein the inside surface of the first grasping tip has a first set of grooved transversal anti-slip elements, and wherein the notch is located adjacent a distal end of the first grasping tip and positioned distal to the first set of grooved transversal anti-slip elements;

a second arm, the second arm comprising a second grasping tip adjacent a distal end of the second arm, wherein an inside surface of the second grasping tip is uniformly covered in a second set of grooved transversal anti-slip elements, wherein a plurality of grooved transversal anti-slip elements of the second set of grooved transversal anti-slip elements are located opposite the notch on the first grasping tip and are configured to interact with an inner edge of the inner conformer ring of the amniotic membrane insert; and a coupling section flexibly connecting the first and second arms at a proximal end, wherein application of an inward pressure on a first and second gripping section on the first and second arms moves the distal end of the first arm and the distal end of the second arm together to reversibly lock the inner conformer ring between the notch and the plurality of grooved transversal anti-slip elements of the second set of grooved transversal anti-slip elements located opposite the notch to prevent the inner conformer ring from moving, and wherein releasing the pressure on the first and second gripping section allows the first and second arms to return to an initial open position and release the inner conformer ring.

2. The forceps according to claim 1, wherein the second arm has the same length as the first arm.

3. The forceps according to claim 1, wherein the notch transverses the width of the first grasping tip.

4. The forceps according to claim 1, wherein the first and second arms extend from the proximal end to create a longitudinal axis of each arm which define a plane of orientation.

5. The forceps according to claim 4, wherein the distal ends of the first and second arms bend downward away from the plane of orientation of the forceps.

6. The forceps according to claim 1, wherein an inner surface of the notch includes one of more grooved transversal anti-slip elements.

7. The forceps according to claim 1, wherein the first and second grasping tips have substantially rounded ends.

8. The forceps according to claim 1, wherein an exterior surface of the first and second gripping section have a plurality of grooved transversal anti-slip elements.

9. The forceps according to claim 1, further comprising a protective cover for the first and second grasping tips.

* * * * *